US010514366B2

(12) United States Patent
Bailey et al.

(10) Patent No.: US 10,514,366 B2
(45) Date of Patent: Dec. 24, 2019

(54) REFRACTIVE INDEX-BASED DETECTION FOR LIQUID CHROMATOGRAPHY USING A MICRORING RESONATOR ARRAY

(71) Applicant: THE BOARD OF TRUSTEES OF THE UNIVERSITY OF ILLINOIS, Urbana, IL (US)

(72) Inventors: Ryan C. Bailey, Urbana, IL (US); James H. Wade, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 366 days.

(21) Appl. No.: 15/508,960

(22) PCT Filed: Sep. 3, 2015

(86) PCT No.: PCT/US2015/048328
§ 371 (c)(1),
(2) Date: Mar. 6, 2017

(87) PCT Pub. No.: WO2016/040106
PCT Pub. Date: Mar. 17, 2016

(65) Prior Publication Data
US 2017/0248560 A1     Aug. 31, 2017

Related U.S. Application Data

(60) Provisional application No. 62/073,491, filed on Oct. 31, 2014, provisional application No. 62/047,156, filed on Sep. 8, 2014.

(51) Int. Cl.
*G01N 30/74*     (2006.01)
*G01N 21/41*     (2006.01)
(Continued)

(52) U.S. Cl.
CPC ......... *G01N 30/74* (2013.01); *G01N 21/4133* (2013.01); *G01N 2021/414* (2013.01);
(Continued)

(58) Field of Classification Search
CPC ...................................................... G01N 30/74
See application file for complete search history.

(56) References Cited

U.S. PATENT DOCUMENTS 4,990,250 A * 2/1991 Hellinger ............... G01N 30/32
                                                                       210/101
5,414,508 A * 5/1995 Takahashi .......... G01N 21/0303
                                                                       204/603
(Continued)

FOREIGN PATENT DOCUMENTS

WO    WO 2005/019798 A2    3/2005

OTHER PUBLICATIONS

Bogaerts, Wim et al., "Silicon Microring Resonators" Laser Photonics Rev. 6, No. 1, 47-73 (2012). (Year: 2012).*
(Continued)

*Primary Examiner* — Paul M. West
(74) *Attorney, Agent, or Firm* — Brinks Gilson & Lione

(57) ABSTRACT

A liquid chromatograph comprising a column coupled to a microring resonator array and methods of using the same are disclosed. The microring resonator array measures the bulk refractive index of the mobile phase and any sample injected onto and separated in the column. While carrying out the methods, the composition of a mobile phase passing through the chromatography column may remain substantially constant (isocratic elution) or it may vary (gradient elution). One or more microrings may comprise a covering to act as a thermal control. In addition, the sensor surface may be modified with some type of capture agent that can interact with one or more components in the sample.

25 Claims, 14 Drawing Sheets

(51) Int. Cl.
 G01N 21/77 (2006.01)
 G01N 30/02 (2006.01)
(52) U.S. Cl.
 CPC .............. *G01N 2021/7789* (2013.01); *G01N 2030/027* (2013.01)

(56) References Cited

U.S. PATENT DOCUMENTS 7,796,262 B1 * 9/2010 Wang ................ G01N 21/7746
 356/436
2003/0125529 A1 * 7/2003 Boschetti ............ B01J 20/0211
 530/417

OTHER PUBLICATIONS

International Search Report and Written Opinion for International Application No. PCT/US2015/048328, dated Nov. 27, 2015 (15 pages).
Wade, James H., et al., "Refractive Index-Based Detection of Gradient Elution Liquid Chromatography Using Chip-Integrated Microring Resonator Arrays," *Analytical Chemistry*, 86(1):913-919 (2014).

* cited by examiner

Microring and Chip Layout

Ring Operation: Resonance Conditions

Resonance: $m\lambda = 2\pi r n_{eff}$

Wavelength Shift in Response to Analyte Elution

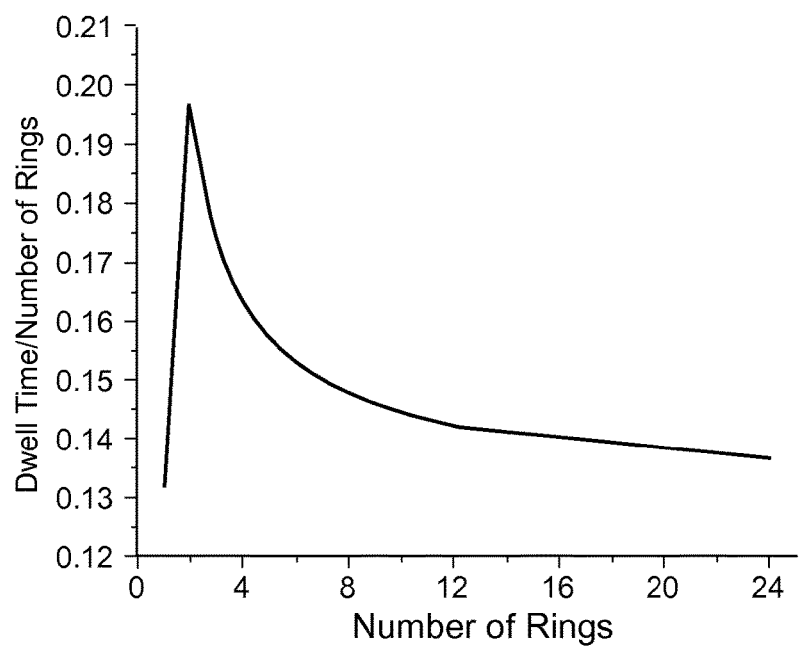

Dwell Time vs Number of Rings

| Equation | y = a + b²x |
| --- | --- |
| Weight | Instrumental |
| Residual Sum of Squares | 268.01539 |
| Pearson's | 0.98948 |
| Adj. R-Square | 0.9989 |

| | | Value | Standard Error |
| --- | --- | --- | --- |
| Mean | Intercept | 0.119 | 0.01185 |
| | Slope | 0.13226 | 0.00127 |

REFRACTIVE INDEX-BASED DETECTION FOR LIQUID CHROMATOGRAPHY USING A MICRORING RESONATOR ARRAY

CROSS-REFERENCE TO RELATED APPLICATIONS

The present application claims the benefit of priority from U.S. Provisional Patent Application No. 62/073,491, filed Oct. 31, 2014, and U.S. Provisional Patent Application No. 62/047,156, filed Sep. 8, 2014, which are incorporated by reference into the present application in their entirety.

STATEMENT REGARDING FEDERALLY SPONSORED RESEARCH OR DEVELOPMENT

This invention was made with government support under contract number 1-DP2-OD002190-01 awarded by the National Institutes of Health, and contract number CHE 12-14081 awarded by the National Science Foundation. The government has certain rights in the invention.

BACKGROUND

1. Field of the Invention

The present disclosure generally relates to liquid chromatography. More particularly, the disclosure relates to detectors configured to measure the bulk refractive index of solutions used in connection with liquid chromatography procedures.

2. Description of the Related Art

Refractive index detectors in high performance liquid chromatography (HPLC) garnered use as a means to analyze samples that lacked strong chromophores in ultraviolet or visible regions, and that were non-fluorescent. The most notable advantages of refractive index detection are: (1) the technique is non-destructive enabling downstream analysis, and (2) refractive index is a concentration dependent bulk property classifying it is as an universal detector (i.e., all compounds with polarizable electrons can be detected under proper conditions). The differential refractometer was one of the earliest implementations of refractive index detection in liquid chromatography and the design has remained popular over the past half-century. The setup contains a sample and a reference flow cell with the cell temperature tightly maintained with a thermostat, commonly at 30° C. or greater.

Comparing changes in bulk refractive index sample versus reference cells of identical mobile phase and temperature enabled sensitivities as low as $10^{-7}$ RIU (refractive index units) and detection limits of approximately 0.1% sample by volume.

However, the reference cell is also the source of major limitations of RI detection for liquid chromatography separations including: (1) the inability to perform gradient separations and (2) extended down time to allow for thermal equilibration of flow cells. Consequently, the limited sensitivity, small dynamic range, and extended equilibration times have limited the use of the differential refractometer and refractive index detection in liquid chromatography to specialty applications, such as lipid, sugar, and protein detection for food analysis.

In the decades following the introduction of refractive index sensing to liquid chromatography, there were multiple attempts to improve upon the original design to increase its applicability. Notable modifications include the elimination of the need to operate at elevated temperature, incorporation of a second column and pumping system enabling analysis of gradient separations, continuous alteration of the laser interrogation angle to adjust for refractive index changes in mobile phase composition to allow gradient separations, and the use of thermooptic, interferometric, and liquid core optical ring resonator (LCORR) methods to increase sensitivity.

However, the design modifications were insufficient to justify significant commercialization and industry adoption, as each improvement only offered a solution to one of the major limitations of refractive index detection.

BRIEF SUMMARY

The present disclosure relates to liquid chromatography systems and methods of using the same. In one embodiment, a liquid chromatography system is disclosed which comprises a chromatography column operatively coupled to a microring resonator array. The microring resonator array is in fluid communication with the chromatography column.

In another embodiment, a liquid chromatography method is disclosed. The method comprises the steps of pumping a mobile phase through a conduit into a chromatography column, injecting a sample comprising one or more components into the mobile phase, the sample being separated into the one or more components in the chromatography column, and allowing the mobile phase and the one or more components to exit the chromatography column during an elution period and enter a flow cell of a detector. The detector comprises a microring resonator array. The method also includes the step of analyzing the one or more components with the microring resonator array.

In an additional embodiment, a liquid chromatography method is disclosed which comprises the steps of pumping a mobile phase through a conduit into a chromatography column, injecting a sample comprising one or more components into the mobile phase, the sample being separated into the one or more components in the chromatography column, allowing the mobile phase and the one or more components to exit the chromatography column during an elution period and enter a flow cell of a detector, and measuring a bulk refractive index of the mobile phase and the one or more components, wherein a composition of the mobile phase changes during the elution period.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

BRIEF DESCRIPTION OF THE SEVERAL VIEWS OF THE DRAWINGS

A detailed description of the invention is hereafter described with specific reference being made to the drawings in which:

FIG. 7A depicts a graph showing an optical scanning instrumentation raster across a detector chip surface probing each microring ring individually;

DETAILED DESCRIPTION

Figure 1A:
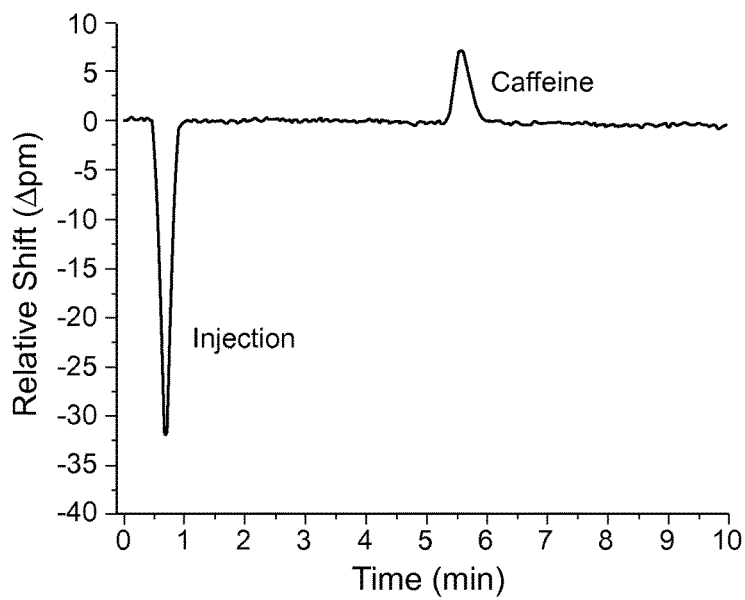
FIG. 1A depicts a graph showing an isocratic separation of caffeine using a microring resonator array.

Various embodiments are described below with reference to the drawings. The relationship and functioning of the various elements of the embodiments may better be understood by reference to the following detailed description. However, embodiments are not limited to those illustrated in the drawings or explicitly described below.

This disclosure relates to certain refractive index-based detectors and their use in identifying and quantifying chemical components. In some embodiments, the presently disclosed refractive index-based detectors may be used in connection with liquid chromatography procedures. For example, the detectors may be used in connection with high performance liquid chromatography (HPLC). HPLC is a process that may be used to separate, identify, and quantify various components of a mixture.

In general, a HPLC device may include a sample injection site or injector, a column, various pumps that may be used to transport solvents and samples through the column, and a detector to analyze effluent from the column. In a typical HPLC process, one or more solvents are placed in one or more reservoirs. One or more pumps are used to transport the one or more solvents through the column at a desired flow rate and in a desired proportion. For example, a first pump may be associated with a first reservoir containing a first solvent and a second pump may be associated with a second reservoir containing a second solvent. A sample containing one or more components may then be injected into the device, whereby the sample mixes with the one or more solvents, which are typically referred to as a mobile phase. The mobile phase may then transport the sample through the column. The volume of sample injected into the device is not critical and is typically in the microliter range, such as from about 1 microliter to about 100 microliters. The pumps are used to create the necessary flow rate and a desired chemical composition of the mobile phase.

While the sample passes through the column, the various components of the sample are separated and in some embodiments, they elute from the column one after the other. Separation of the various components may occur due to certain physical interactions between a given component and a material inside of the column. For example, HPLC columns typically comprise a sorbent or stationary phase which interacts with the various components of the sample. Generally, the speed at which a certain component emerges from the column (also known as its "retention time") depends upon its chemical structure, the mobile phase, and the sorbent in the column.

There are numerous columns available that can be used in connection with HPLC. Columns may comprise a specific sorbent or combinations of two or more sorbents. The sorbents may be selected based upon the components to be separated. In some embodiments, the sorbents can be hydrophobic or hydrophilic. The sorbents may also comprise different particle sizes. For example, the sorbents may have particle sizes ranging from about 2 μm to about 50 μm. The sorbents may comprise silica and/or various polymers, for example. In some embodiments, the column may be heated to facilitate the separation process. The size of the column is not critical and any size column is contemplated by the present disclosure. In some embodiments, a column may have a diameter of about 2 mm to about 5 mm and a length of about 25 mm to about 300 mm.

As the separated components elute from the column, they pass into a flow cell of the detector and over the detector, which may be beneath the flow cell. The detector analyzes the components and mobile phase as they pass through the flow cell and it may send an electrical signal to a computer, for example, to convert the electrical signal into a data plot that may identify the particular component and quantify the same. Upon exiting the flow cell of the detector, the mobile phase may be collected or sent to waste, for example. If the mobile phase comprises a separated component, it may be collected so the component may be further analyzed or stored, for example.

The mobile phase used in connection with the HPLC device is not particularly limited and may be selected by one of ordinary skill in the art depending upon the mixture to be separated. Typical mobile phases include water and one or more organic solvents, such as methanol and/or acetonitrile. Mobile phases may also include various salts or acids. The composition of the mobile phase can affect the time at which a specific component elutes from the column. For example, if a component is highly hydrophobic, it may not elute from the column in a timely manner if the mobile phase comprises only water so acetonitrile, for example, may be added to the mobile phase to cause the hydrophobic component to elute more quickly.

In some HPLC procedures, the mobile phase may be held constant, meaning that its composition does not change over time or the course of the separation experiment. This may be referred to as isocratic elution. For example, a mobile phase may comprise 50% water and 50% acetonitrile. Throughout the entire separation process in an isocratic elution using this mobile phase, the mobile phase will always comprise about 50% water and about 50% acetonitrile in an isocratic elution. In contrast, in a gradient elution, the composition of the mobile phase changes over the course of the separation process. For example, at the beginning of the process, the mobile phase may contain about 10% acetonitrile and about 90% water. The HPLC device can be programmed to run for about 30 minutes, for example, and over the course of the 30 minutes, the amount of acetonitrile in the mobile phase may increase so that at the end of the 30 minute period, the mobile phase may comprise about 90% acetonitrile and about 10% water. The change from 10% acetonitrile to 90% acetonitrile can occur gradually over the 30 minute time period or it may occur in steps, whereby, for example, at the 10 minute mark, the amount of acetonitrile increases from about 10% to about 50% and, at the 25 minute mark, the amount of acetonitrile increases from about 50% to about 90%. All different types of gradients are intended to be covered by the present disclosure as well as all different types of solvents. The foregoing are merely examples used to illustrate the concepts disclosed herein.

As previously noted, a HPLC device may be in fluid communication with solvent/mobile phase reservoirs. Chemical injection pumps are used to pump the solvents from the reservoirs into the HPLC device and the column. In some aspects, a conduit may be provided in each reservoir leading to a mixing chamber and a conduit may carry the mixed solvent (mobile phase) from the mixing chamber into, and through, the column. In an isocratic process, the pumps may be programmed to take the same amount of solvent from each reservoir throughout the entire separation process so the mobile phase stays substantially constant. In a gradient elution, the pumps may be programmed to vary the amount of one or more of the solvents being pumped into the HPLC device and column throughout the separation process such that the composition of the mobile phase changes throughout the course of the separation.

In certain embodiments, the detector is a microcavity photonic device. For example, the detector may comprise a passive silica chip with a plurality of microring resonators disposed thereon. Microcavity photonic devices are a subset of high-Q optical sensors that allow for label free detection of analyte due to the sensitivity to the local dielectric surrounding the sensor surface. While exact size and geometries may vary, the core structure of such devices is generally circular, allowing light to be repeatedly coupled around the structure's circumference, thereby increasing the effective optical pathlength.

Silicon photonic microring resonators are a type of microcavity device including an array of any number of individually addressable microring resonators. The device also includes a linear waveguide adjacent to each microring resonator, and interference between photons traversing the linear waveguide and those circumnavigating the microring only allow photons within a narrow spectral window to couple into the microring. The resonance condition for a microring geometry is described by:

$$m\lambda = 2\pi r n_{eff} \quad \text{(Equation 1)}$$

where m is any integer, $\lambda$ is wavelength, r is the radius of the microring, and $n_{eff}$ is the effective refractive index near the sensor surface. Based on Equation 1, the resonant wavelength will track with changes in the local refractive index. The effective refractive index sampled by each microring resonator extends from the microstructure surface to a 1/e distance of about 63 nm.

Figure 6A:
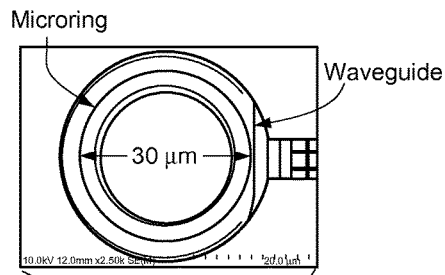
FIG. 6A depicts a representative detector chip layout.
Figure 6A:
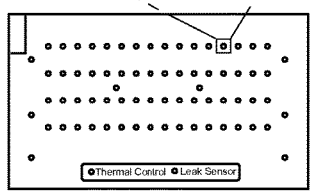
Figure 6B:
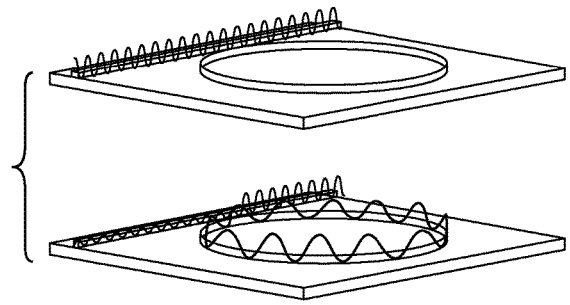
FIG. 6B depicts light propagating down a linear waveguide.
Figure 6C:
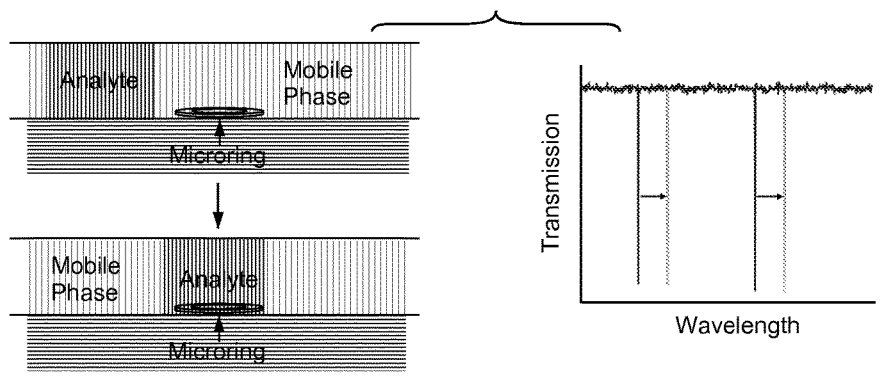
FIG. 6C depicts a representative example of wavelength shift in response to analyte elution.

FIGS. 6A-6C illustrate detector chip layout and operation principles. In FIG. 6A, the 4 mm×6 mm silicon-on-insulator chips contain 132 individually addressable microrings in an array format. A scanning electron microscopy (SEM) image of one of the microrings with adjacent waveguide is provided. FIG. 6B shows that light propagating down the linear waveguide via total internal relectance (TIR) will couple into the microring under specific resonance conditions, as described by Equation 1. Light coupling into the rings results in a dip in transmission across a small spectral window ($\Delta\lambda \leq 1$ pm). With respect to FIG. 6C, while typically operated with a modified sensor surface, the microring resonator is sensitive to bulk refractive index changes. When the bulk refractive index surrounding the ring (evanescent field with 1/e distance of 63 nm) changes, the resonant wavelength will shift by approximately 63 nm/RIU.

In one embodiment, the detector comprises a silicon photonic microring resonator array. The detector and/or silica chip may comprise any number of microring resonators, such as from about 1 microring resonator to more than 132 microring resonators.

In some embodiments, thermal controls may be integrated into one or more of the microring resonators. For example, one or more of the microring resonators may be covered with a covering. The covering may comprise a fluoropolymer, for example. If a microring resonator comprises a covering, it would not directly contact the fluid being analyzed. In some embodiments, one of the microring resonators comprises a covering and in other embodiments, more than one microring resonator comprises a covering, such as about 4 microring resonators or about one half of the total number of microring resonators. By integrating thermal controls into one or more of the microring resonators, the need to operate under tightly controlled thermal conditions is eliminated, thereby obviating extended detector equilibration wait times.

In some embodiments, the surface of one or more of the microring resonators may be modified. For example, a surface of a microring resonator may be modified such that it includes an organic moiety, a silane, polyethylene glycol, an antibody, or some other type of capture agent that can interact with one or more of the components in the sample. The surface of one or more of the microring resonators may be modified to include any biological or chemical recognition elements, such as dendrimers, polymers, hydrophobic constituents, hydrophilic constituents, ion exchange resins, or constituents having cationic and/or anionic moieties.

The detector may be configured to measure the bulk refractive index of the solution, which includes the mobile phase and any components that the mobile phase may comprise. Bulk refractive index of the solution may be differentiated from measuring a differential refractive index because when measuring differential refractive index, two different sample cells would need to be analyzed and the differential refractive index would be calculated based upon the difference of the refractive index measured for each individual cell. When measuring bulk refractive index in accordance with certain embodiments of the present disclosure, only one cell is necessary.

While certain prior art liquid chromatography procedures may use detectors capable of measuring a differential refractive index of a sample, the prior art detectors have a very limited dynamic range. For example, detectors in the prior art may have dynamic ranges up to 600 μRIU. In contrast, the presently disclosed microring resonators may have dynamic ranges of greater than 190,000 μRIU.

Microring resonator arrays, such as silicon photonic microring resonator arrays, can track large fluctuations in refractive index, as described above, and they can also operate under ambient conditions. The increased dynamic range enables operation of the detector across a wide spectrum of refractive indices, such as moving from an aqueous to organic mobile phase. Mobile phase gradients are reproducible independent of temperature fluctuations and enable gradient separations using a refractive index sensing modality, which is currently not offered in the prior art.

In some embodiments, the microring resonator, or an array of microring resonators, is the only detector used in connection with the liquid chromatography process and in other embodiments, additional detectors may be used in connection with the microring resonator or microring resonator array. For example, a HPLC device may comprise a microring resonator array in addition to a detector selected from the group consisting of a UV-absorbance detector, a fluorescence detector, an evaporative-light-scattering detector, a mass spectrometer, and any combination thereof.

Unlike commercial detectors, the interfacing of HPLC with microring resonator arrays does not require a reference flow channel for subtraction, instead relying on the previously discussed integrated thermal controls. The presently disclosed microring resonators disclosed herein are capable of operating under ambient conditions without the extended equilibration time required by prior art detectors and they also eliminate the need to acquire reference data and sample data simultaneously. As such, the HPLC-microring resonator platform is capable of performing gradient separations. Preferential interaction of analytes with an optionally modified array surface can impart a two dimensional separation capability to the detector. Further, due to a small footprint (about 3 mm×5 mm), the chip comprising the microring resonators can be integrated into lab-on-a-chip devices, which are commonly known in the art.

Examples

Unless otherwise indicated, all reagents were purchased from Sigma-Aldrich (St. Louis, Mo.) and used as received. Ibuprofen liquid gel capsules (NDC 11673-122-80) were purchased from Target Corporation (Minneapolis, Minn.). Phosphate buffered saline (PBS) was reconstituted from Dulbecco's PBS at 10 mM and pH balanced to either about 7.4 or about 2.3. Oxalic acid dehydrate, DL-malic acid, and succinic acid were prepared at various concentrations in 10 mM PBS pH 2.3. Ibuprofen and simvastatin were prepared in a 50:50 mixture of deionized (DI) water and HPLC-grade acetonitrile. Caffeine was prepared in DI water.

The microring resonators, sensor array chips, optical scanning instrumentation, and instrument accessories were purchased from Genalyte (San Diego, Calif.). Briefly, detector fabrication was performed on an 8 inch silicon wafer via UV photolithography and reactive ion etching. The wafer was then diced into individual 3 mm×5 mm chips, and an amorphous fluoropolymer cladding layer was spun coated over the entire chip surface. Annular openings were then photolithographically made over all active sensor rings. Each chip contained 132 individually addressable microring resonators, 64 of which had an annular opening. Rings that remained coated with the cladding layer remained inert under varying surface conditions and served as thermal control rings. See FIGS. 7A-7C for scanning electron microscopy (SEM) images of the microring and waveguide structures and schematics of the sensor geometry.

Figure 7B:
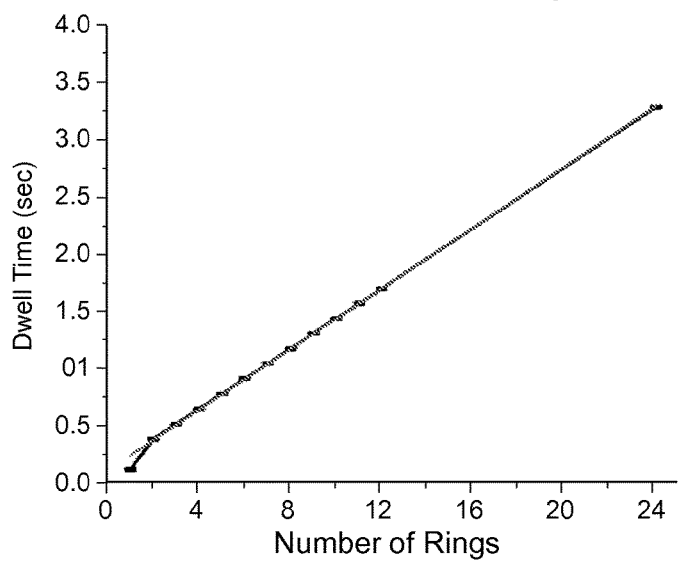
FIG. 7B depicts a graph showing a linear relationship between dwell time and the number of active microrings.
Figure 7C:
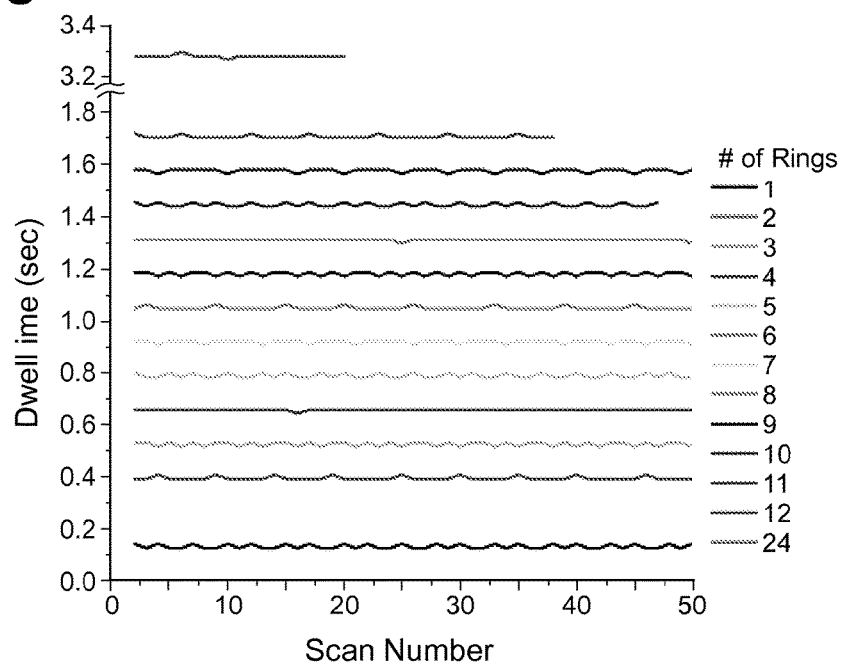
FIG. 7C depicts a graph showing an additional representation of dwell time across a series of scans.

In FIG. 7A, the optical scanning instrumentation rasters across the chip surface probing each microring ring individually. The minimum scan rate is 0.13 seconds. The dwell time between data points reaches a maximum near 0.20 seconds and decreases as the number of rings increases. With respect to FIG. 7B, the laser rasters linearly across the sensor surface, resulting in a linear relationship between dwell time (i.e., time between data points for an individual microring) and the number of active rings. FIG. 7C is another representation of dwell time across a series of scans that indicates the reproducibility of the dwell time.

Proprietary software from Genalyte (Maverick Host Control, M1 Host ver 11.0) offered the selection of 1 to 132 rings. Typically, 8 bare rings were selected as active sensor rings, and 4 covered rings were selected as thermal controls.

Before use, sensor chips were initially rinsed with a 10 second rinse of acetone then isopropanol in order to remove a protective photoresist coating. The chips were then cleaned using a piranha solution (3:1 $H_2SO_4$:30% $H_2O_2$) for 40 seconds. After cleaning, the chips were sonicated in ethanol for 5 minutes and dried under nitrogen.

A tunable external cavity diode laser centered on 1550 nm was used to serially probe each microring individually, scanning across a 12 nm spectral window. Light was coupled into and out of linear waveguides via grating couplers specific to each microring. The transmittance of light as a function of wavelength was monitored with a charge-coupled device (CCD). Dips in the transmittance were associated with light coupling into the microcavity and relative shifts in the resonant wavelength were used to measure small changes in refractive index. The optical scanning instrumentation enables sub-picometer (pm) precision and a noise floor of approximately 0.3 pm, corresponding to a bulk refractive index sensitivity of about $4.8 \times 10^{-6}$ based on the determined relationship of 63 nm/RIU (see FIGS. 2A-2C). Relative shifts were monitored in real time at a scan rate of 0.13 rings/sec. See FIGS. 8A and 8B for additional scan rate information.

Figure 8A:
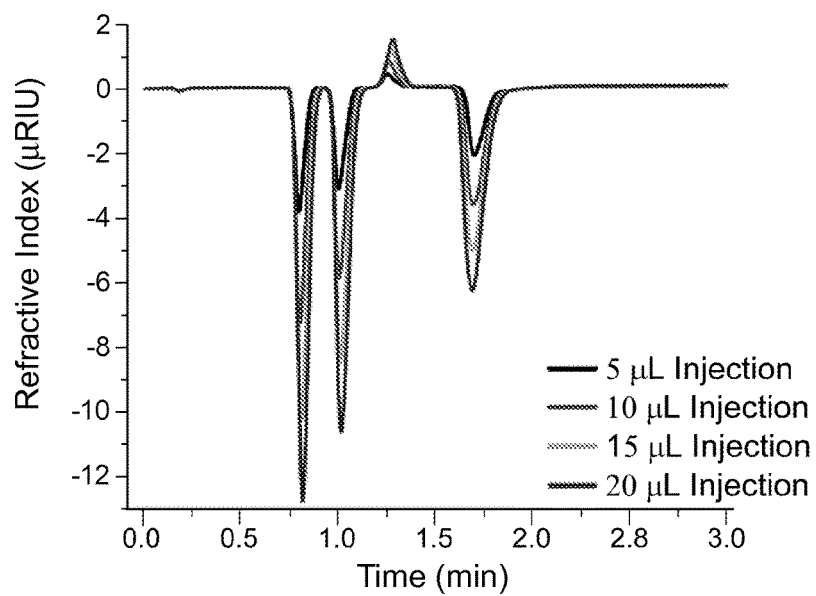
FIG. 8A depicts a graph showing data from a commercial refractive index detector measuring malic acid, oxalic acid, and succinic acid.
Figure 8B:
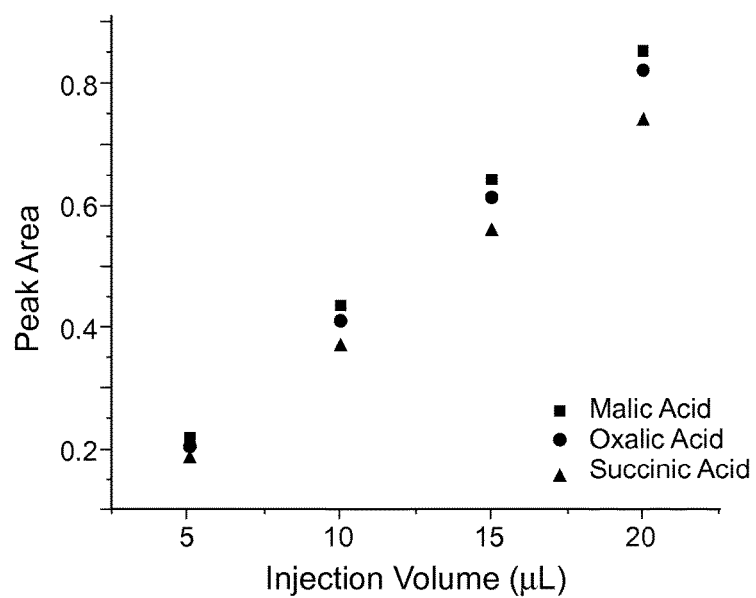
FIG. 8B depicts a graph showing a plot of peak area versus injection volume of the separation depicted in FIG. 8A.

Specifically, FIG. 8A shows various injection volumes from 5 to 20 μL of malic acid, succinic acid, and succinic acid, all at 1.00 mg/mL dissolved in 10 mM PBS pH 2.3. The column used for separations was a Hypersil Gold polar-capped C18 column. FIG. 8B shows a plot of peak area versus injection volume and also shows a linear relationship with slopes varying slightly dependent upon the analyte. The results are very similar to those obtained using the microring resonator arrays as the detector.

With respect to the HPLC procedures, chromatographic separations were performed using a Dionex Ultimate® 3000 Binary Analytical System (Thermo Fisher Scientific, Waltham, Mass.) equipped with a HPG-3200SD pump, WPS-3000SL analytical autosampler with 100 μL sample loop, TCC-3000SD column compartment, MWD-3000 diode array detector, and RefractoMax 521 refractive index detector. Mobile phase composition for isocratic separations included (1) 10 mM PBS pH 2.3, (2) 10 mM PBS pH 7.4, and (3) 90:10 DI water to acetonitrile. Gradient methods comprised (1) an initial mobile phase of 90:10 water:acetonitrile and ending with 0:100 water:acetonitrile with a linear gradient and (2) an initial mobile phase of DI water and ending with 1 M NaCl.

HPLC columns included (1) Acclaim 120 C18 column with 3 μm particle size, pore size of 120 Å, and dimensions of 4.6 mm×150 mm and (2) Hypersil GOLD® aQ polar endcapped C18 column with 1.9 µm particle size, pore size of 175 Å, and dimensions of 4.6 mm×150 mm. Flow rate, when operated in standalone mode, was 0.600 mL/min and 0.100 mL/min for the LC-microring resonator interface, unless otherwise noted. The column oven was set to 40° C. and 25° C. for the Acclaim C18 and Hypersil Gold columns, respectively. The RefractoMax detector was maintained at 30° C.

For interface of the microring resonator arrays with the HPLC device, the chip sensor was placed into an aluminum cartridge holder, and a 0.007 inch biaxially-oriented polyethylene terephthalate (Mylar®) gasket and a polytetrafluoroethylene (Teflon®) cartridge top for fluid delivery. The outlet from the HPLC was connected to a 0.25 mm flangeless ¼-28 to ZDV 10-32 PEEK low pressure union to convert from HPLC to microring resonator fluidic fittings and a ¼-28 nut was screwed directly into the Teflon cartridge top. The microring resonator platform limited flow rates to 0.100 mL/min. See FIG. 10 for a representative depiction.

Figure 10:
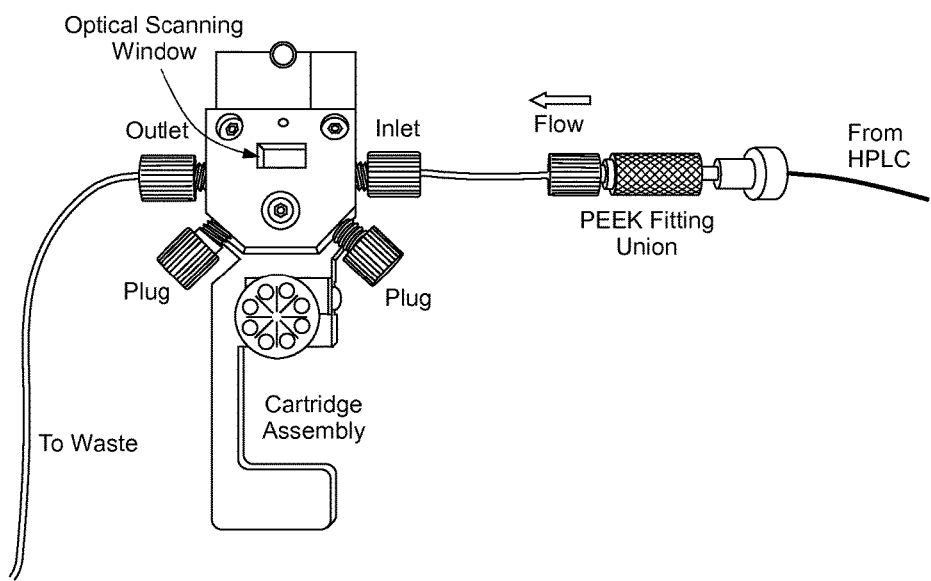
FIG. 10 illustrates a detector setup according to an embodiment of the present disclosure.

Specifically, FIG. 10 shows the outlet from a HPLC diode array detector connected to the inlet of the cartridge assembly via a 0.25 mm flangeless ¼-28 to ZDV 10-32 PEEK low pressure union. PEEK and stainless steel tubing types were used for HPLC fluid delivery and PTFE tubing was used for the connection from the union to the cartridge assembly. In order from top to bottom, the cartridge assembly includes an aluminum cartridge holder, a SOI detector chip, a Mylar fluidic gasket, and a Teflon cartridge top. The cartridge assembly allows for multiple flow configuration and two PEEK plugs are used to block the unused fluidic channel. The optical scanning window allows for the sequential interrogation of each microring using a tunable diode laser.

All data analysis for the microring resonator platform was performed using Origin Pro 9.0. Signal response was thermally controlled by subtracting 2 or more rings covered with fluoropolymer. Thermally controlled data was subsequently averaged, and the average response represents between 4 and 32 bare rings.

To prove the utility of the presently disclosed detectors, such as the presently disclosed microring resonator array detectors, in reference to established prior art liquid chromatography detectors, the inventors performed isocratic separations on well-characterized analytes in addition to gradient elution of analytes in pure buffer and a more complex matrix of a dissolved liquid gel capsule.

Figure 5:
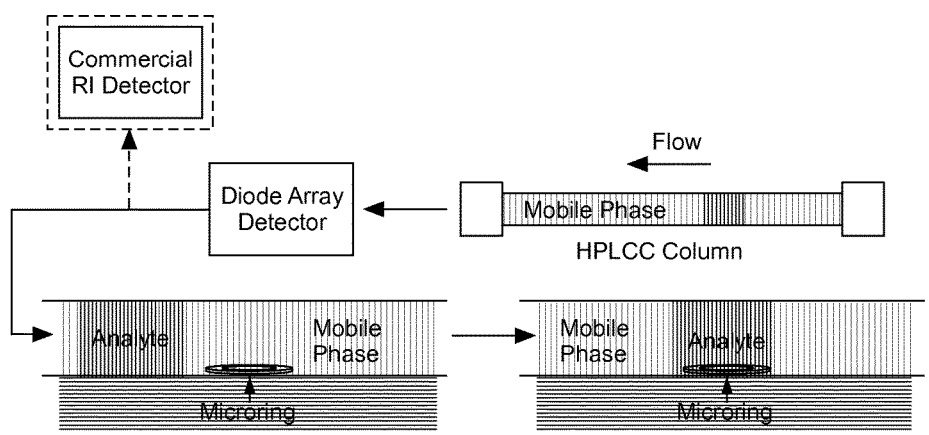
FIG. 5 depicts an outline of a HPLC device according to an embodiment of the present application.

An example of an interface between HPLC and a microring resonator array platform is depicted in FIG. 5. For a comparison to conventional refractive index detectors, isocratic separation methods were used. For all runs, UV/Vis absorption data was acquired followed by downstream detection using the microring resonator array platform. For comparison, the effluent was directed to a commercial refractive index detector. A caffeine solution in water is a common standard for verification of system integrity and is commonly employed as an internal standard.

Figure 1B:
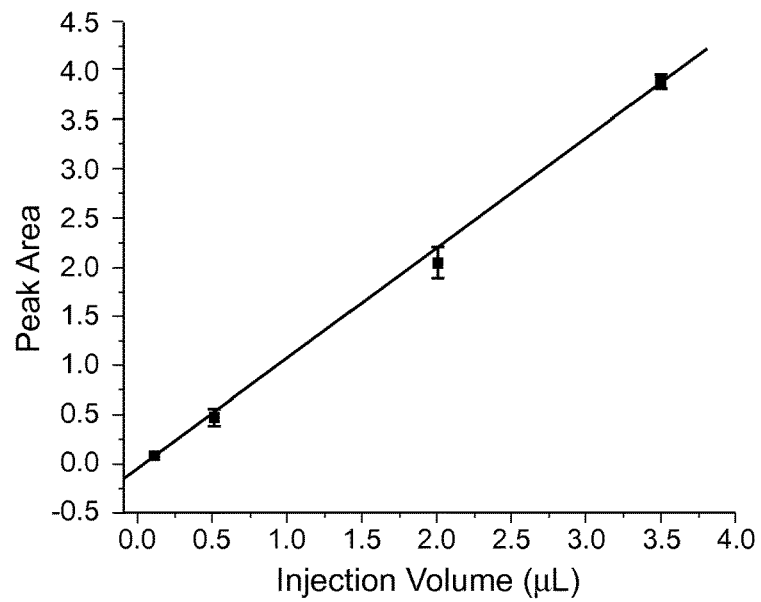
FIG. 1B depicts a graph showing peak area versus injection volume of the caffeine separation.

FIG. 1A depicts a chromatogram corresponding to detection of a 10 mg/mL caffeine at various injection volumes using an Acclaim™ 120 C18 column and a mobile phase of about 90:10 deionized (DI) water:acetonitrile. Peaks corresponding to the injection volume and caffeine were baseline resolved at the smallest injection volume of about 0.1 µL, and the peak area is linearly related to the mass of caffeine injected onto the column (see FIG. 1B). The plot peak area versus injection volume shows the reproducibility of peak area and linearity of mass injected onto the column and detector response (N=3 and error bars are standard deviation (SD)).

Figure 1C:
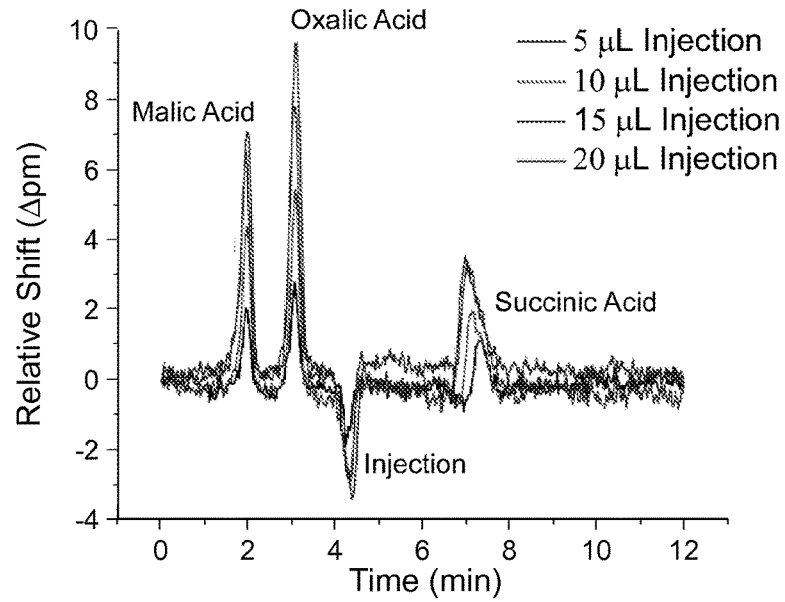
FIG. 1C depicts a graph showing various injection volumes of malic acid, succinic acid, and succinic acid.
Figure 1D:
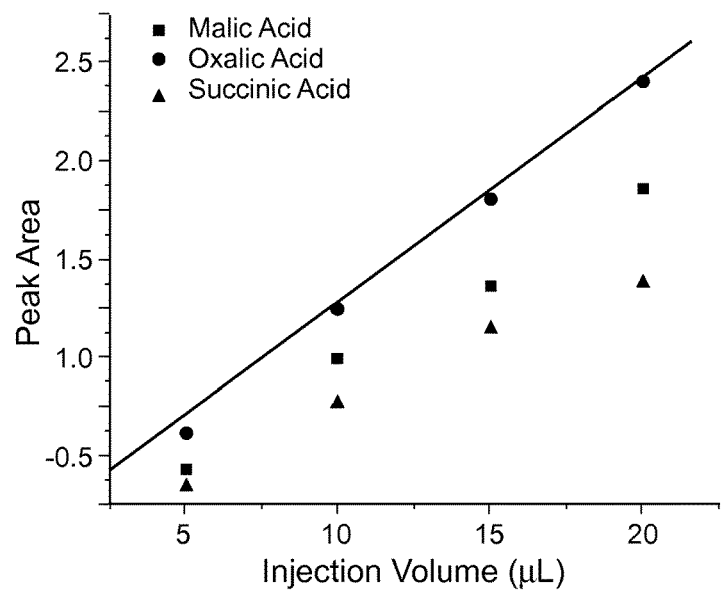
FIG. 1D depicts a graph showing peak area versus injection volume of the separation shown in FIG. 1C.

The second isocratic separation was malic acid, oxalic acid, and succinic acid in 10 mM phosphate buffered saline (PBS) pH 2.3. Peaks for each of the analytes and the injection were baseline resolved. FIG. 1C shows sample injections (all at about 1.66 mg/mL dissolved in 10 mM PBS pH 2.3) ranging from about 5 to about 20 µL, and the separation was performed using the Hypersil GOLD aQ™ polar capped C18 column. Peak area correlated strongly with mass injected onto the column for each analyte, showing a linear relationship with slopes varying slightly depending upon the analyte, as shown in FIG. 1D. In comparison to refractive index data from a commercial detector, the noise levels are slightly higher and the sensitivities are comparable. FIG. 8 shows the separation using the commercial detector.

Early in the development of HPLC, gradient mobile phases were introduced to increase elution time and sharpen later-eluting peaks. Gradient methods improve the efficiency of method development and minimize the need for complicated sample preparation due to interference species. In addition, large molecules, such as proteins and oligonucleotides, are difficult to resolve with isocratic methods due to widely altered retention times in response to minor changes in mobile phase. The constantly changing composition was successfully applied to visual, UV/Vis, and fluorescence based detection as nearly all mobile phase components were optically transparent in the 200-800 nm window. However, the gradual move from aqueous to organic mobile phase components (e.g., water to methanol) results in a refractive index well beyond the dynamic range of conventional detectors. The reported linear dynamic range of the RefractoMax™ detector is 600 µRIU. In comparison, the ΔRIU of methanol versus water at 25° C. and 550 nm is 3,200 µRIU.

Figure 2A:
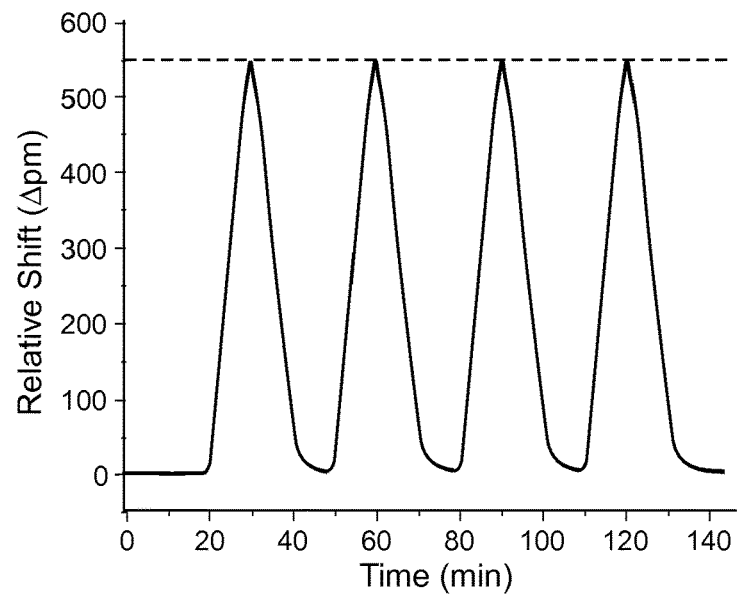
FIG. 2A depicts a graph showing a series of four identical salt gradients.

In order to demonstrate the dynamic range of the presently disclosed microring resonator array detector, a variety of gradients were used. FIG. 2A demonstrates the reproducibility of a linear gradient from DI water to 1 M NaCl and returning to DI water. A thermally referenced reproducible gradient is a requirement for gradient elutions under ambient conditions. Controlling for temperature enables decoupling reference and sample gradients temporally and eliminating the need for a reference lane. From a practical standpoint, an initial reference gradient run could optionally be performed and subtracted from all subsequent runs using the same sensor array and mobile phase solutions.

Figure 2B:
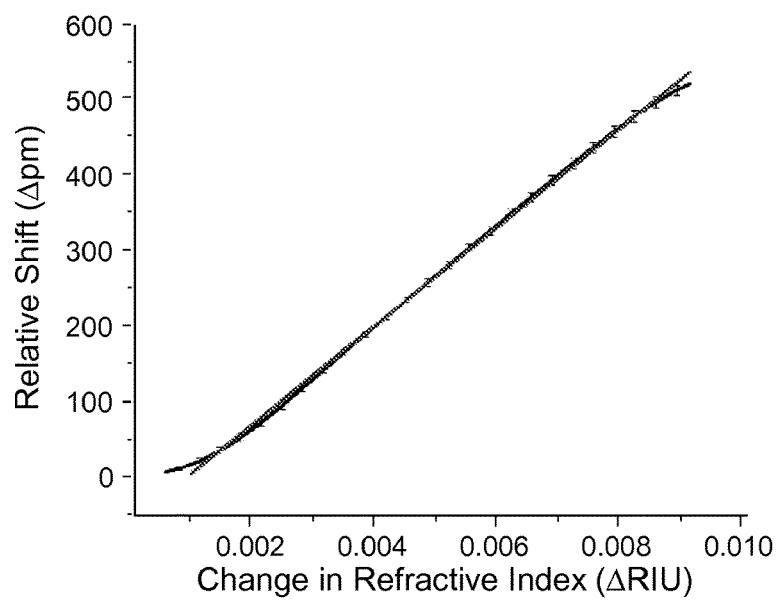
FIG. 2B depicts a graph showing the relative shift in wavelength versus change in refractive index.

One commonly used metric to assess the merits of an optical detector and compare different types of detectors is the detector response to a known bulk refractive index shift. The metric provides a reliable baseline sensitivity for a bare sensor surface. FIG. 2B shows the relationship between relative shifts in the resonant wavelength as a function of the shift in bulk refractive index. The adjusted r-squared value is greater than 0.997 with a slope of 63.3+/−0.1 nm/RIU. Based on the baseline of about 0.30 pm, the bulk refractive index sensitivity is approximately $4.8\times10^{-6}$ RIU. Notably, bulk refractive index shifts do not account for the extreme surface sensitivity utilized in other applications of microring resonator arrays with modified surfaces. Modification of the silicon surface with silanes, biomolecules, polymers, or other surface chemistries, as discussed above, is contemplated to enhance sensor sensitivity to as low as about $1\times10^{-9}$ RIU.

Figure 2C:
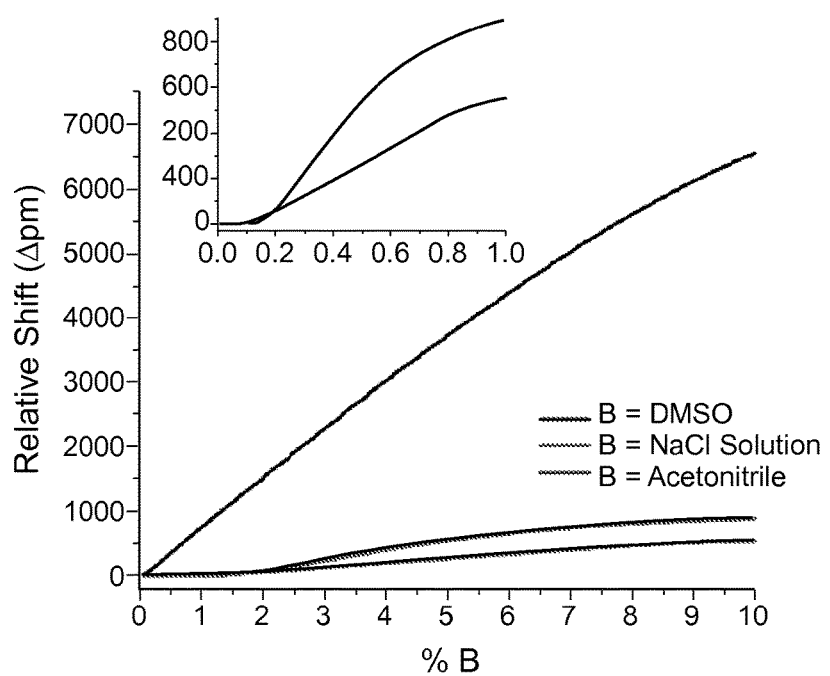
FIG. 2C depicts a graph showing gradients for 3 different mobile phase compositions.

One of the most notable characteristics of the microring resonator arrays for the application of gradient elutions is the extended dynamic range. FIG. 2C shows gradient elutions for three mobile phase gradients: 90:10 water:acetonitrile to acetonitrile, water to 1 M NaCl, and water to dimethylsulfoxide (DMSO). Clearly, DMSO demonstrates the most striking relative wavelength shift of over 7 nm. A 7 nm shift represents a change in bulk refractive index shift of over 100,000 µRIU, offering a dynamic range of 3 orders of magnitude over commercial instruments. Additionally, the scanning instrumentation for the microring resonator arrays performed a 12 nm wavelength sweep for every data point on each microring within the array. Therefore, the theoretical dynamic range is at least as large as 190,000 µRIU, a value sufficient to handle all relevant mobile phases for conventional gradient elutions.

Figure 3A:
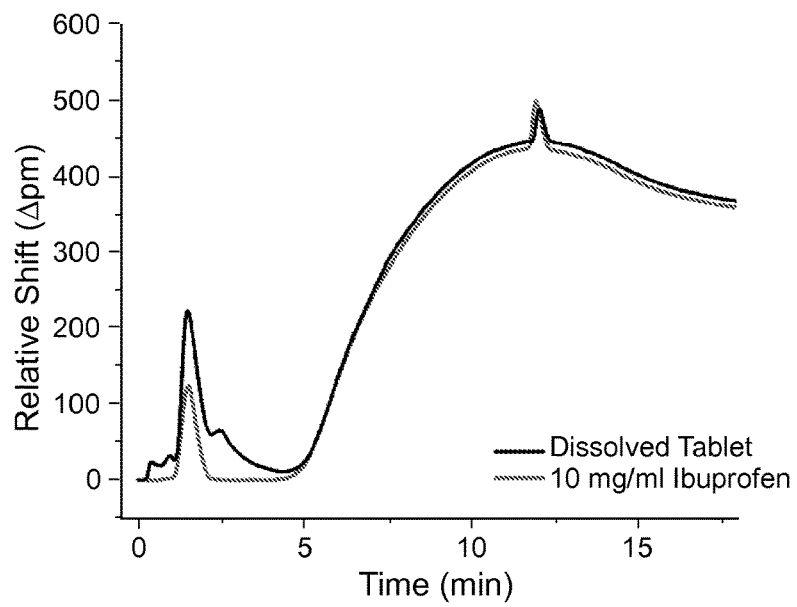
FIG. 3A depicts a graph showing a separation of ibuprofen and simvastatin.
Figure 3B:
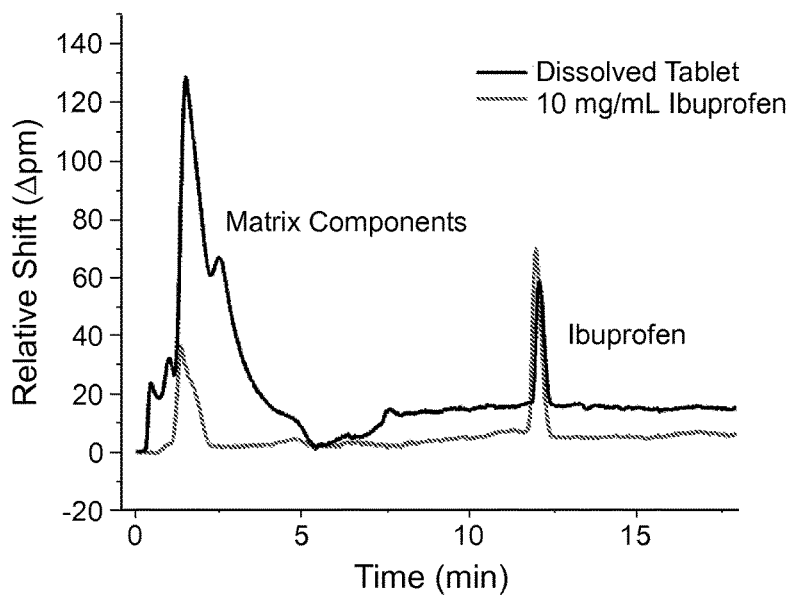
FIG. 3B depicts a graph showing data from the separation of FIG. 3A referenced to an identical gradient with no injection.

While the reproducibility and wide dynamic range of microring resonator arrays in response to rapid, large shifts and refractive index in the form of gradients were evident, the present inventors also determined whether small changes in refractive index associated with the elution of analytes could be resolved from a simultaneous signal increase in response to changes in the mobile phase composition. As with demonstration of isocratic methods, well characterized, model analytes, namely ibuprofen and simvastatin, were used to demonstrate detection of analytes in gradient elutions. The gradient employed was intentionally simplistic to ensure that all sensogram changes were due to injection, mobile phase changes, and/or sample elution. The gradient from 90:10 water:acetonitrile to acetonitrile over 30 minutes showed clearly resolved peaks for the two model analytes. A large injection volume of 100 µL was used to demonstrate the upper limit of analyte signal. The samples were dissolved in a 50:50 water:acetonitrile solution before injection. FIG. 3A shows a 100 µL injection of 2.5 mg/mL ibuprofen and simvastatin in 50:50 water:acetonitrile and FIG. 3B shows data from FIG. 3A referenced to an identical gradient with no injection.

Figure 4A:
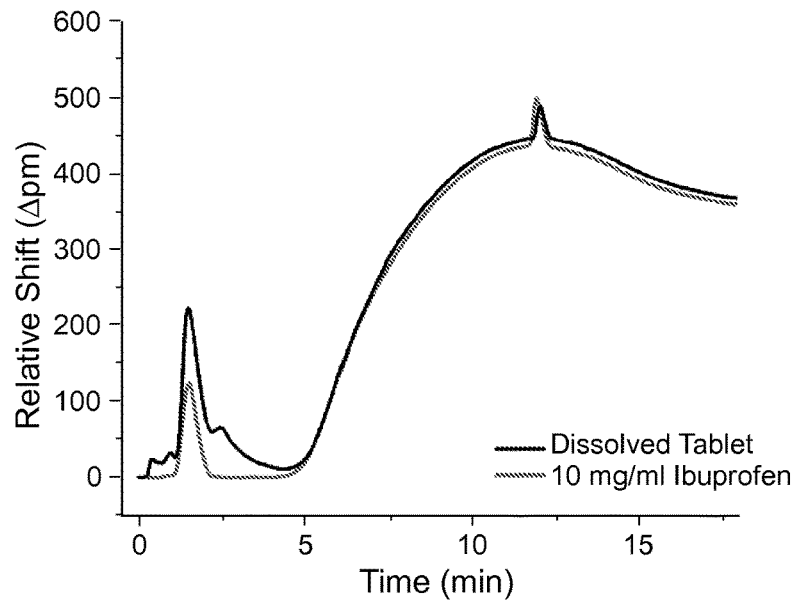
FIG. 4A depicts a graph showing a separation of an ibuprofen liquid gel capsule.

The use of refractive index based detection is highly advantageous due to its ability to act as a universal detector responding to essentially all analytes of sufficient concentration. As such, one application of refractive index detection is in the chromatographic separation of complex sample matrices. In order to demonstrate the application of microring resonator arrays for the analysis of a more complex sample, the inventors tested an ibuprofen liquid gel capsule dissolved in a 50:50 water:acetonitrile solution. The dissolved capsule was a notably less complex matrix than commonly studied samples such as serum, cell lysate, or waste water. One advantage of using the capsule was that it contained a stable component already analyzed (i.e., ibuprofen) as well as uncharacterized matrix components. In addition to ibuprofen, the liquid gel capsule also contained FD&C green no. 3 (an organic dye), gelatin, mineral oil, pharmaceutical ink (composed of alcohols, shellac, titanium dioxide, and propylene glycol), polyethylene glycol, potassium hydroxide, water, sorbitan, and sorbitol. FIG. 4A shows the separation of capsule components dissolved in a 50:50 water:acetonitrile solution. Specifically, FIG. 4A shows a 20 µL injection of an ibuprofen liquid gel capsule dissolved in 20 mL of 50:50 water:acetonitrile. A 20 µL injection of 10 mg/mL ibuprofen stock is provided for reference.

Figure 4B:
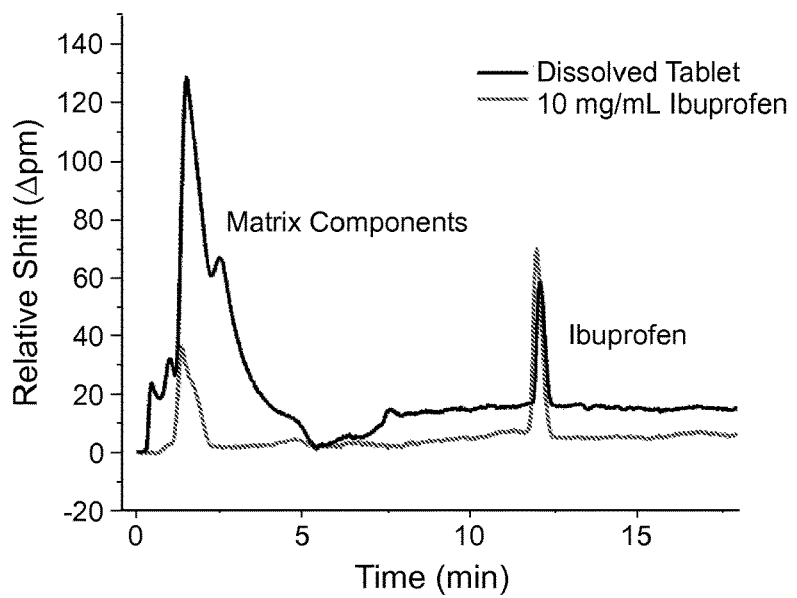
FIG. 4B depicts a graph showing data from the separation of FIG. 4A referenced to an identical gradient.
Figure 9:
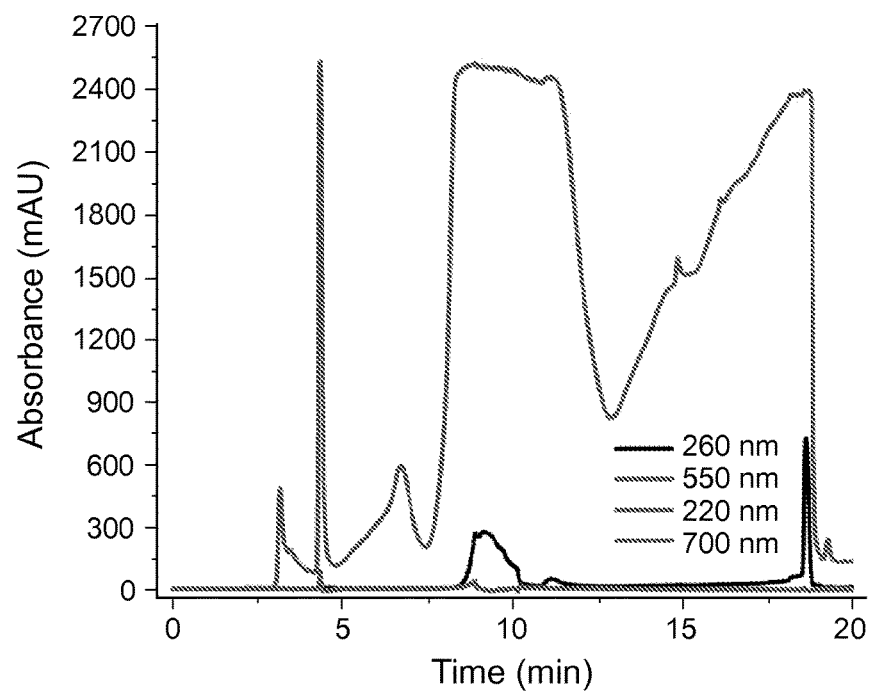
FIG. 9 depicts a graph showing UV/VIS data for a separation of an ibuprofen liquid gel capsule.

In comparison to a 10 mg/mL ibuprofen solution, matrix components result in a broad response surrounding the injection peak. Ibuprofen peaks are comparable by comparing 10 mg/mL stock versus the dissolved capsule. FIG. 4B depicts the same separation with a subtracted reference of a 20 µL injection of 50:50 water:acetonitrile. For comparison, UV/Vis data acquired for the identical separation is provided in FIG. 9. Specifically, with respect to FIG. 9, a 20 µL injection of an ibuprofen liquid gel capsule dissolved in 20 mL of 50:50 water:acetonitrile was monitored at 220 nm, 260 nm, 550 nm, and 700 nm. The microring resonator array appears is shown to be well-suited for identification of ibuprofen in the sample matrix.

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a device" is intended to include "at least one device" or "one or more devices."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. A liquid chromatography system comprising:
   a chromatography column operatively coupled to a microring resonator array, wherein the microring resonator array is in fluid communication with the chromatography column, and wherein the microring resonator array comprises a thermal control.

2. The system of claim 1, further comprising one or more pumps configured to pump a mobile phase through the chromatography column.

3. The system of claim 1, wherein the microring resonator array comprises silicon photonic microring resonators.

4. The system of claim 1, wherein the microring resonator array comprises a flow cell.

5. The system of claim 1, wherein the column comprises one or more sorbents.

6. The system of claim 1, wherein the microring resonator array comprises a dynamic range of at least about 190,000 µRIU.

7. The system of claim 1, wherein the array comprises from about 2 to about 132 microring resonators.

8. The system of claim 7, wherein a surface of at least one of the microring resonators is modified.

9. The system of claim 1, wherein the microring resonator array is disposed on a silica chip.

10. The system of claim 1, further comprising a linear waveguide adjacent the microring resonator array.

11. A liquid chromatography method comprising:
pumping a mobile phase through a conduit into a chromatography column;
injecting a sample comprising one or more components into the mobile phase, the sample being separated into the one or more components in the chromatography column;
allowing the mobile phase and the one or more components to exit the chromatography column during an elution period and enter a flow cell of a detector, wherein the detector comprises a microring resonator array; and
analyzing the one or more components with the microring resonator array, wherein a composition of the mobile phase changes during the elution period.

12. The method of claim 11, wherein the chromatography column comprises one or more sorbents.

13. The method of claim 11, wherein one or more pumps are configured to pump the mobile phase in varying concentrations and the sample through the conduit and the chromatography column during the elution period.

14. The method of claim 11, wherein the detector comprises from about 2 to about 132 microring resonators.

15. The method of claim 14, wherein a surface of at least one of the microring resonators is modified.

16. The method of claim 11, wherein the method is carried out at ambient temperature without heating.

17. The method of claim 11, wherein the microring resonator array measures a bulk refractive index of the mobile phase and the one or more components.

18. The method of claim 11, wherein the microring resonator array comprises a thermal control.

19. The method of claim 11, wherein the microring resonator array comprises a dynamic range of at least about 190,000 µRIU.

20. A liquid chromatography method comprising:
pumping a mobile phase through a conduit into a chromatography column;
injecting a sample comprising one or more components into the mobile phase, the sample being separated into the one or more components in the chromatography column;
allowing the mobile phase and the one or more components to exit the chromatography column during an elution period and enter a flow cell of a detector; and
measuring a bulk refractive index of the mobile phase and the one or more components, wherein a composition of the mobile phase changes during the elution period, and wherein the detector comprises a microring resonator array.

21. The method of claim 20, wherein the composition of the mobile phase changes according to a predetermined gradient.

22. A liquid chromatography system comprising:
a chromatography column operatively coupled to a microring resonator array, wherein the microring resonator array is in fluid communication with the chromatography column, and wherein the microring resonator array comprises a dynamic range of at least about 190,000 µRIU.

23. A liquid chromatography method comprising:
pumping a mobile phase through a conduit into a chromatography column;
injecting a sample comprising one or more components into the mobile phase, the sample being separated into the one or more components in the chromatography column;
allowing the mobile phase and the one or more components to exit the chromatography column during an elution period and enter a flow cell of a detector, wherein the detector comprises a microring resonator array; and
analyzing the one or more components with the microring resonator array, wherein the microring resonator array measures a bulk refractive index of the mobile phase and the one or more components.

24. A liquid chromatography method comprising:
pumping a mobile phase through a conduit into a chromatography column;
injecting a sample comprising one or more components into the mobile phase, the sample being separated into the one or more components in the chromatography column;
allowing the mobile phase and the one or more components to exit the chromatography column during an elution period and enter a flow cell of a detector, wherein the detector comprises a microring resonator array; and
analyzing the one or more components with the microring resonator array, wherein the microring resonator array comprises a thermal control.

25. A liquid chromatography method comprising:
pumping a mobile phase through a conduit into a chromatography column;
injecting a sample comprising one or more components into the mobile phase, the sample being separated into the one or more components in the chromatography column;
allowing the mobile phase and the one or more components to exit the chromatography column during an elution period and enter a flow cell of a detector, wherein the detector comprises a microring resonator array; and
analyzing the one or more components with the microring resonator array, wherein the microring resonator array comprises a dynamic range of at least about 190,000 µRIU.

* * * * *